United States Patent
Van Maris et al.

(10) Patent No.: US 11,326,172 B2
(45) Date of Patent: May 10, 2022

(54) POLYPEPTIDES WITH IMPROVED ARABINOSE TRANSPORT SPECIFICITY

(71) Applicant: DSM IP ASSETS B.V., Heerlen (NL)

(72) Inventors: Antonius Jeroen Adriaan Van Maris, Stockholm (SE); Jacobus Thomas Pronk, Delft (NL); Maarten Dirk Verhoeven, Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/763,394

(22) PCT Filed: Nov. 12, 2018

(86) PCT No.: PCT/EP2018/080876
§ 371 (c)(1),
(2) Date: May 12, 2020

(87) PCT Pub. No.: WO2019/096718
PCT Pub. Date: May 23, 2019

(65) Prior Publication Data
US 2021/0002651 A1    Jan. 7, 2021

(30) Foreign Application Priority Data

Nov. 14, 2017 (EP) ..................................... 17201608
Nov. 28, 2017 (EP) ..................................... 17203961

(51) Int. Cl.
| | | |
|---|---|---|
| *C12N 15/00* | (2006.01) | |
| *C12N 15/70* | (2006.01) | |
| *C12N 9/90* | (2006.01) | |
| *C12P 7/06* | (2006.01) | |
| *C12N 15/52* | (2006.01) | |
| *C07K 14/435* | (2006.01) | |
| *C12N 9/12* | (2006.01) | |
| *C12P 7/14* | (2006.01) | |

(52) U.S. Cl.
CPC ............ *C12N 15/52* (2013.01); *C07K 14/435* (2013.01); *C12N 9/12* (2013.01); *C12N 9/90* (2013.01); *C12P 7/14* (2013.01)

(58) Field of Classification Search
CPC .... Y02E 50/10; C12P 7/10; C12P 7/06; C12P 7/14; C12N 9/0006; C12N 15/81; C12N 9/90; C12N 15/70; C12N 15/00; C12Y 503/01003; C12Y 504/02; C12Y 501/03001
USPC ............... 435/254.2, 161, 440, 72, 193, 194
See application file for complete search history.

(56) References Cited

FOREIGN PATENT DOCUMENTS

WO    2014/195520 A2    12/2014

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Reznicek, O. et al., "Improved xylose uptake in *Saccharomyces cerevisiae* due to directed evolution of galactose permease Gal2 for sugar con-consumption", Journal of Applied Microbiology, pp. 99-111, vol. 119.
Nijland, Jeroen G. et al., "Engineering of an endogenous hexose transporter into a specific D-xylose transporter facilitates glucose-xylose co-consumption in *Saccharomyces cerevisiae*", Biotechnology for Biofuels, 2014, pp. 1-11, vol. 7, No. 168.
Wang, Chengqiang et al., "Identification of Important Amino Acids in Gal2p for Improving the L-arabinose Transport and Metabolism in *Saccharomyces cerevisiae*", Frontiers in Microbiology, Jul. 21, 2017, vol. 8.
Caballero, Antonio and Juan Luis Ramos, "Enhancing ethanol yields through D-xylose and L-arabinose co-fermentation after construction of a novel high efficient L-arabinose-fermenting *Saccharomyces cerevisiae* strain", Microbiology, 2017, pp. 442-452, vol. 163.
Shin, Hyun Yong et al., "An engineered cryptic Hxt11 sugar transporter facilitates glucose-xylose co-consumption in *Saccharomyces cerevisiae*", Biotechnology for Biofuels, 2015, pp. 1-13, vol. 8, No. 176.
Becker, Jessica and Eckhard Boles, "A Modified *Saccharomyces cerevisiae* Strain That Consumes L-Arabinose and Produces Ethanol", Applied and Environmental Microbiology, Jul. 2003, pp. 4144-4150, vol. 69, No. 7.
International Search Report of International Patent Application No. PCT/EP2018/080876 dated Jan. 15, 2019.

* cited by examiner

*Primary Examiner* — Robert B Mondesi
*Assistant Examiner* — Mohammad Y Meah
(74) *Attorney, Agent, or Firm* — McBee Moore & Vanik IP, LLC; Susan McBee; Chester Moore

(57) ABSTRACT

The invention relates to a variant of a parent polypeptide which is preferably a hexose transporter, wherein the variant comprises an amino acid sequence which, when aligned with the amino acid sequence of SEQ ID NO: 1, comprises a substitution of amino acids N376 and T89, the positions of said amino acids being defined with reference to the amino acid sequence of SEQ ID NO: 1. Said polypeptide is suitable in the production of ethanol from arabinose-rich biomass such as corn stover and corn starch.

14 Claims, 6 Drawing Sheets

Specification includes a Sequence Listing.

POLYPEPTIDES WITH IMPROVED ARABINOSE TRANSPORT SPECIFICITY

CROSS-REFERENCE TO RELATED APPLICATIONS

This application is a National Stage entry of International Application No. PCT/EP2018/080876, filed 12 Nov. 2018, which claims priority to European Patent Application No. 17203961.2, filed 28 Nov. 2017, and European Patent Application No. 17201608.1, filed 14 Nov. 2017.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-527000_ST25.txt" created on 11 May 2020, and 33,619 bytes in size) is submitted concurrently with the instant application, and the entire contents of the Sequence Listing are incorporated herein by reference.

BACKGROUND

Field

The invention relates to variant polypeptides with improved arabinose transport specificity and reduced glucose transport activity, a recombinant yeast comprising a nucleic acid sequence encoding said polypeptides, and their use to produce a fermentation product such as ethanol.

Description of Related Art

By functionally replacing fossil-fuel derived compounds, microbial production of chemicals and transport fuels can contribute to a transition to a sustainable, low-carbon global economy. The total industrial production of fuel ethanol, which reached ca. 100 billion liters in 2015, is predicted to increase further. The yeast *Saccharomyces cerevisiae* is the established microbial cell factory for conversion of starch and sucrose derived hexose units to ethanol, as it combines a high ethanol yield and productivity with robustness under process conditions. Efforts in yeast strain improvement and process optimization of corn-starch and cane sugar based bioethanol production have further improved product yields and productivity. Furthermore, intensive metabolic and evolutionary engineering studies have yielded yeast strains capable of efficiently fermenting the pentose sugars xylose and arabinose, thus paving the way for yeast based 'second-generation' bioethanol production from lignocellulosic hydrolysates.

The hexose transporter Gal2 is known to mediate arabinose transport (Becker J, Boles E. 2003, A modified *Saccharomyces cerevisiae* strain that consumes L-Arabinose and produces ethanol, Appl Environ Microbiol. 69: 4144-4150). However, the affinity for the respective pentose sugars is approximately 10 to 100 times lower than for the respective hexose sugars. The lack of a dedicated xylose or arabinose transporter in recombinant yeast cells thus limits the capacity for co-utilization of hexoses and pentoses in sugar mixtures, and prohibits a high pentose catabolic flux. As a consequence, conversion of biomass sugars may be considered bi-phasic: in the first phase, a relatively fast conversion of hexoses (glucose) takes place, while in the second phase, which starts when the hexoses have been exhausted from the medium, pentose fermentation commences, but at a far lower rate as compared to the rate of hexose conversion.

It is therefore a long-felt desire to express arabinose specific sugar transporters, i.e. no glucose interference (arabinose specificity) and high affinity to arabinose in order to maintain the ability to convert hexoses at approximately the same level.

DETAILED DESCRIPTION

Figure 1:
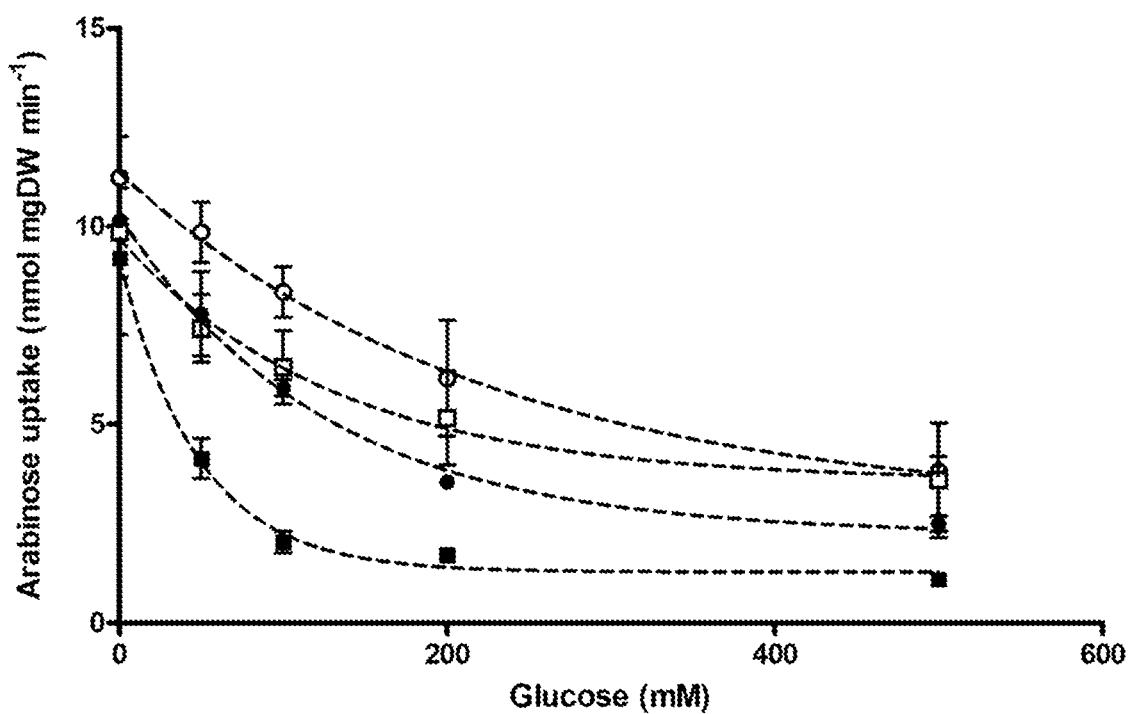
FIG. 1. Uptake experiments using 50 mM [14C-] L-arabinose in the presence of a range of D-glucose concentrations using strain DS68625 expressing Gal2 variants: N376T+T89I (open circles), N376T (closed circles), T89I (open squares) and Gal2 wild-type (closed squares).
Figure 2:
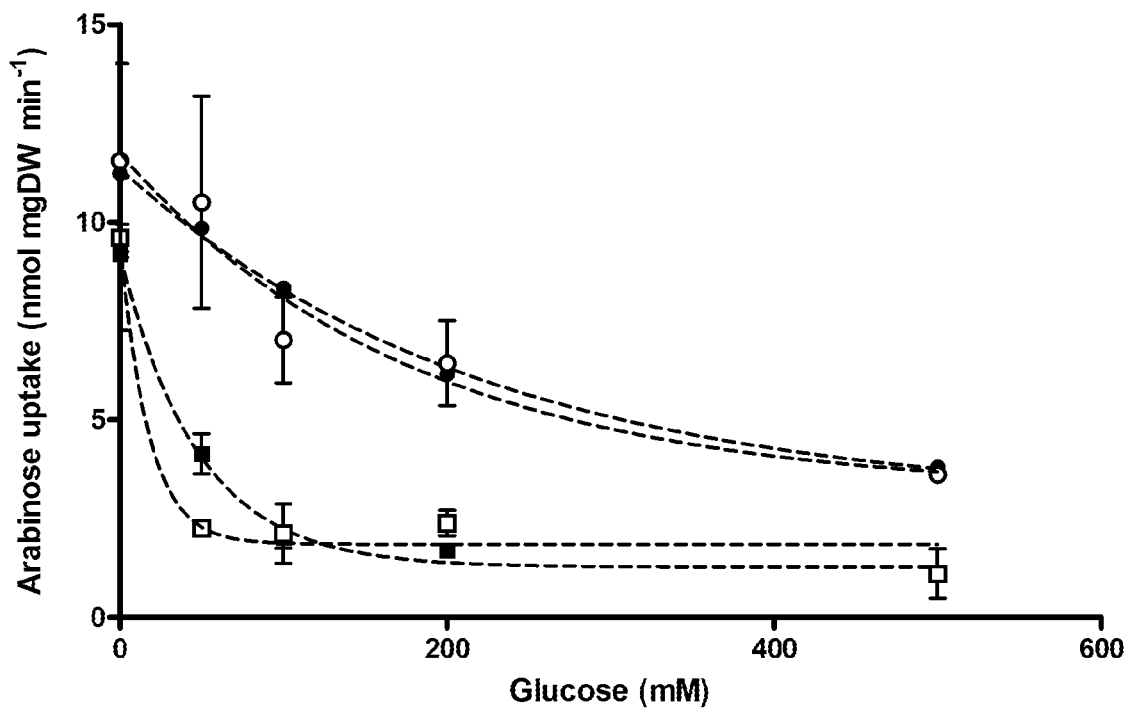
FIG. 2. Uptake experiments using 50 mM [$^{14}$C-] L-arabinose in the presence of a range of D-glucose concentrations using strain DS68625 expressing Gal2 variants: N376T+T89I (open circles), N376T (closed circles), T89I (open squares) and Gal2 wild-type (closed squares).
Figure 3A:
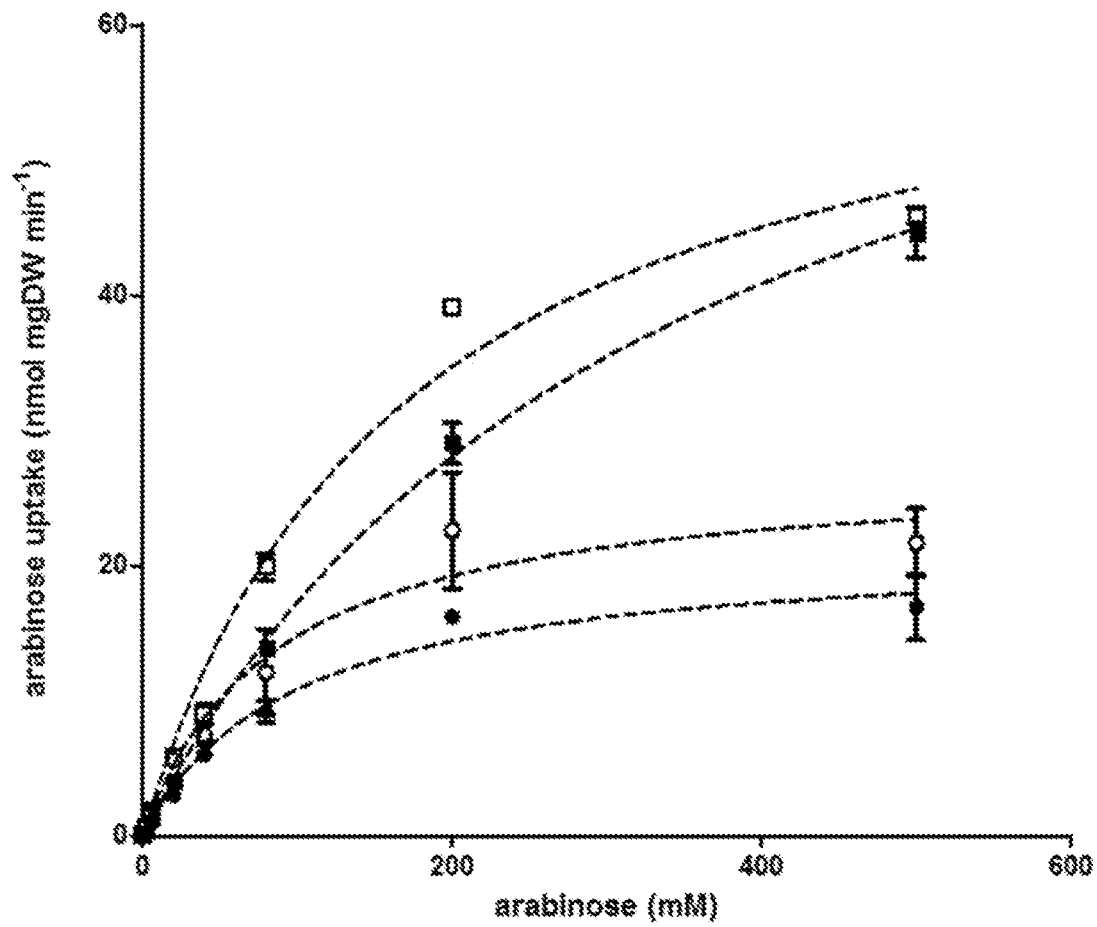
FIGS. 3A-3D. Uptake experiments using various concentrations of [$^{14}$C-] L-arabinose (top) or [$^{14}$C-] D-glucose (bottom) to determine $K_m$ and $V_{max}$ of strain DS68625 expressing Gal2 variants: T89I (open circles), N376T+T89I (closed circles), N376T (open squares), Gal2 wild-type (closed squares), N376S (closed diamonds) and N376I (open diamonds).
Figure 3B:
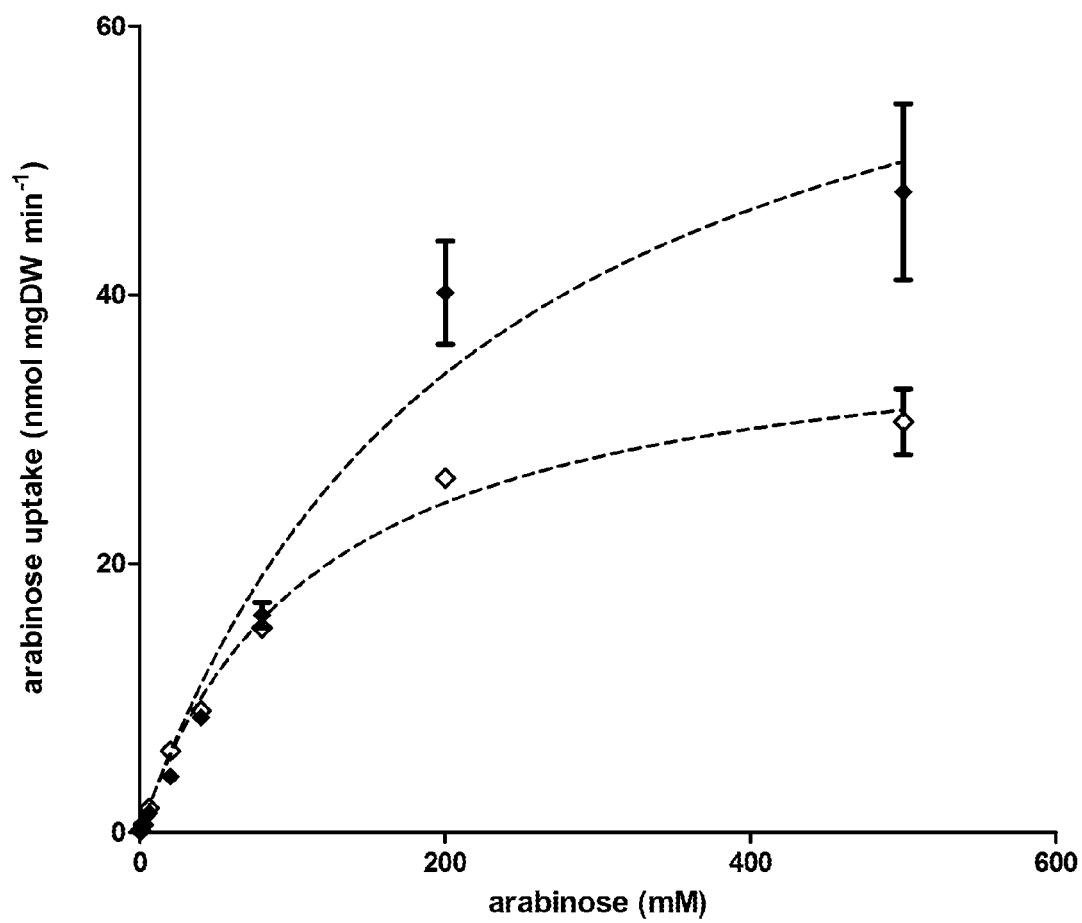
Figure 3C:
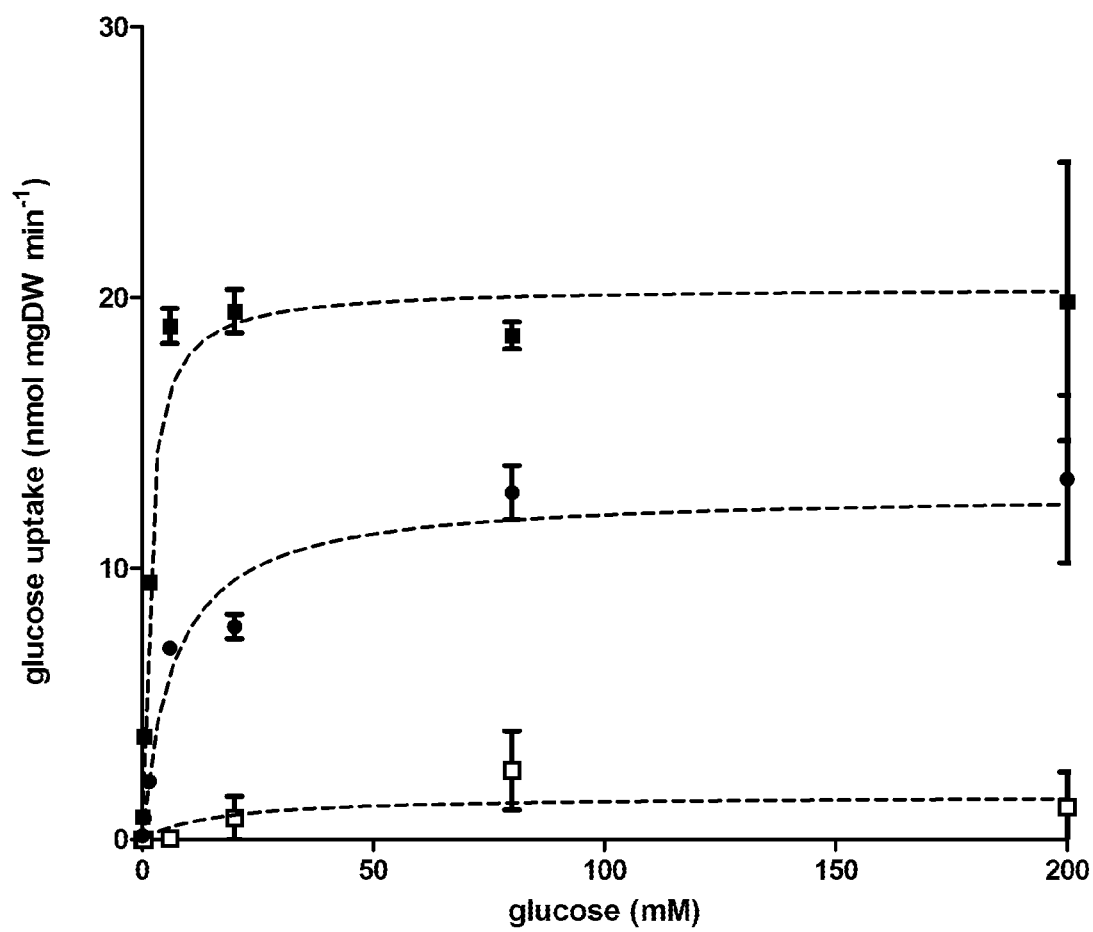
Figure 3D:
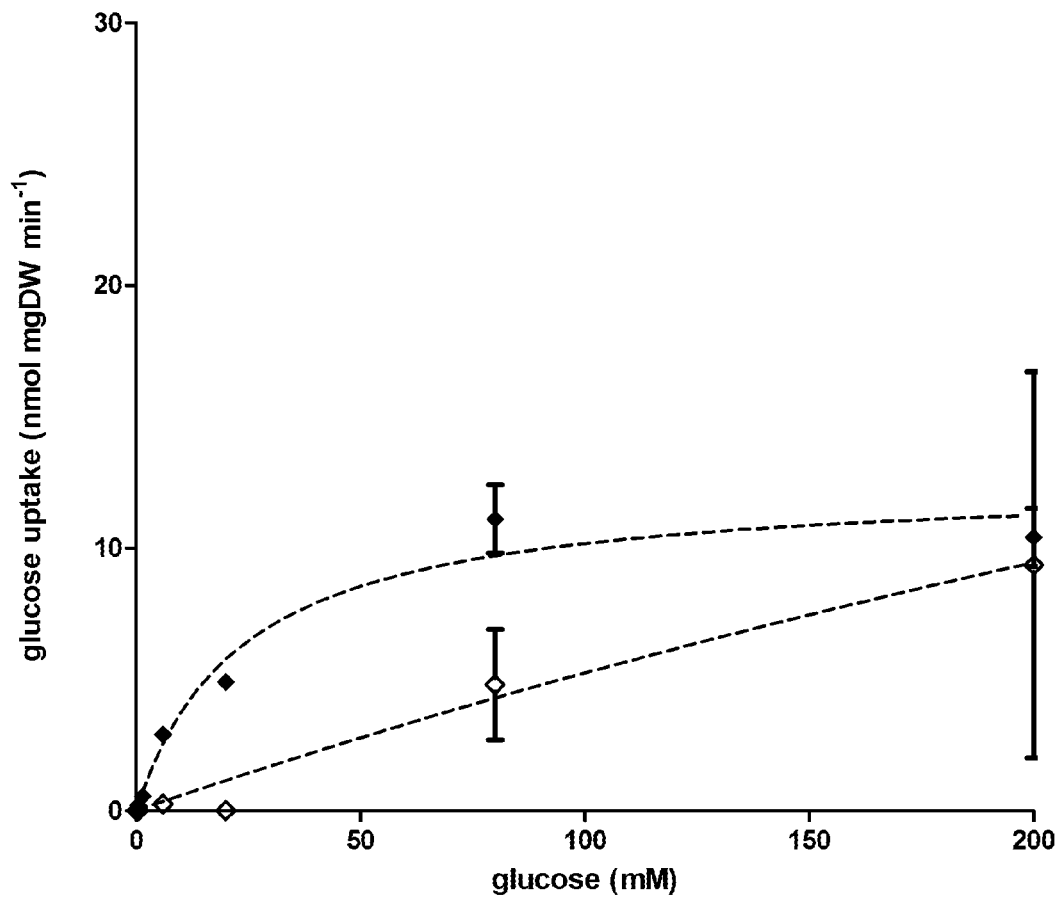

An object of the invention is to provide novel variant hexose transport polypeptides having reduced glucose affinity. Another object of the invention is to provide novel variant hexose transport polypeptides having high affinity for arabinose. One or more of these objects are attained according to the invention.

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an amino acid" may mean one amino acid or more than one amino acid.

Amino acid sequence aligned with the amino acid sequence set out in SEQ ID NO: X (when referring to a variant polypeptide) means that the variant amino acid sequence and the amino acid sequence set out in SEQ ID NO: X are aligned by a suitable method which allows comparison of the sequences with each other and identifications of the positions in the amino acid sequence of the variant wherein either the same amino acid is present (identical position), or another amino acid is present (substitution), or one or more extra amino acids are present (insertion or extension) or no amino acid is present (deletion or truncation) if compared with the amino acid sequence set out in SEQ ID NO: X.

A suitable method allowing comparison of two amino acid sequence may be any suitable Pairwise Sequence Alignment method known to those skilled in the art, preferably a Global Pairwise Sequence Alignment method. A preferred Global Pairwise Sequence Alignment method is the EMBOSS Needle method based on the Needleman-Wunsch alignment algorithm (aiming at finding the optimum alignment (including gaps) of the two sequences along their entire length) (Needleman, S. B. and Wunsch, C. D. (1970) J. Mol. Biol. 48, 443-453) as described herein. In one embodiment the amino acid sequence is aligned with the amino acid sequence set out in SEQ ID NO: x using the NEEDLE program from the EMBOSS package, using EBLOSUM62 as a substitution matrix, with a gap-open penalty of 10 and a gap extension penalty of 0.5.

A "yeast" or "yeast cell" as defined herein is a yeast suitable for genetic manipulation and which may be cultured at cell densities useful for industrial production of a target product. A yeast or yeast cell may be found in nature or a cell derived from a parent cell after genetic manipulation or classical mutagenesis.

The term "control sequence" as used herein refers to components involved in the regulation of the expression of a coding sequence in a specific organism or in vitro. Examples of control sequences are transcription initiation sequences, termination sequences, promoters, leaders, signal peptides, propeptides, prepropeptides, or enhancer sequences; Shine-Delgarno sequences, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion.

The term "culturing" refers to a method of multiplying microorganisms in a nutrient medium and under conditions suitable for the growth and/or propagation of said microorganism and/or the production of a compound of interest by the microorganism. These methods are known in the art. When the microorganism is able to express/produce a compound of interest, for example, the microorganisms may be cultured by shake flask culturing, small-scale or large-scale fermentation (including continuous, batch, fed-batch, or solid state fermentations) in laboratory or industrial fermenters performed in a suitable medium and under conditions allowing the compound of interest to be expressed and/or isolated. Typically, the culturing will comprise a growth phase mainly directed to formation of biomass and a production phase mainly directed to production of the compound of interest. The growth phase and production phase may overlap to some extent. A suitable nutrient medium comprises carbon sources, nitrogen sources and additional compounds (such as inorganic salts (e.g. phosphate), trace elements and/or vitamins) (see, e. g., Bennett, J. W. and LaSure, L., eds., More Gene Manipulations in Fungi, Academic Press, Calif., 1991) and can be performed under aerobic or anaerobic conditions.

The term "derived from" also includes the terms "originates from," "obtained from," "obtainable from," "isolated from," and "created from," and typically indicates that one specified material finds its origin in another specified material or has features that can be described with reference to the another specified material. As used herein, a substance (e.g., a nucleic acid molecule or polypeptide) "derived from" a microorganism preferably means that the substance is native to that microorganism.

The term "expression" includes any step involved in the production of (a) polypeptide(s) including, but not limited to, transcription, post transcriptional modification, translation, post-translational modification, and secretion. A reduction or abolishment of production of B means a limitation to x % or less B produced via enzymatic conversion of A. This can be achieved with an enzyme/protein/cell/gene as described herein. An increase in production of B means an increase of at least x % B produced via enzymatic conversion of A compared to the amount B obtained in a process using a non-modified cell/wild type protein/enzyme/gene. Reduction or increase of gene expression can be measured by various methods, such as e.g. Northern, Southern or Western blot technology as known in the art. The terms "increase of activity" or "overexpression" are used interchangeably herein.

An expression cassette comprises a polynucleotide coding for a polypeptide, operably linked to the appropriate control sequences which allow for expression of the polynucleotide in a cell or in vitro.

The expression cassette may be an autonomously replicating vector (e.g plasmid), i. e., a vector the replication of which is independent of genome replication. Alternatively, the cassette may be one which, when introduced into the cell, is fully or partially integrated into the genome of the cell. In the latter cases it may comprise one or more targeting sequences to direct integration into the genome.

The expression cassette may or may not contain one or more selectable markers, which permit easy selection of transformed cells.

The term "polypeptide fragment" is defined herein as a polypeptide having one or more amino acids deleted from the amino and/or carboxyl terminus of the parent polypeptide.

The term "mature polypeptide" is defined herein as a polypeptide in its final form(s) and is obtained after translation of a mRNA into polypeptide, post-translational modifications of said polypeptide in or outside the cell. Post-translational modification include N-terminal processing, C-terminal truncation, glycosylation, phosphorylation and removal of leader sequences such as signal peptides, propeptides and/or prepropeptides as defined herein by cleavage.

The term "naturally-occurring" as used herein refers to processes, events, or products that occur in their relevant form in nature. By contrast, "not naturally-occurring" refers to processes, events, or products whose existence or form involves the hand of man. The term "non-naturally occurring" is herein synonymous with "man-made". Generally, the term "naturally-occurring" with regard to polypeptides or nucleic acids can be used interchangeable with the term "wild-type" or "native". It refers to polypeptide or nucleic acids encoding a polypeptide, having an amino acid sequence or polynucleotide sequence, respectively, identical to that found in nature. Naturally occurring polypeptides include native polypeptides, such as those polypeptides naturally expressed or found in a particular cell. Naturally occurring polynucleotides include native polynucleotides such as those polynucleotides naturally found in the genome of a particular cell. Additionally, a sequence that is wild-type or naturally-occurring may refer to a sequence from which a variant or a synthetic sequence is derived.

The term "nucleic acid construct" is herein referred to as a nucleic acid molecule, either single-or double-stranded, which is derived from a naturally occurring gene or which has been modified to contain segments of nucleic acid which are combined and juxtaposed in a manner which would not otherwise exist in nature. Nucleic acid constructs can be isolated, synthetically made of mutagenized. The term nucleic acid construct is synonymous with the term "expression cassette" when the nucleic acid construct contains all the control sequences required for expression of a coding sequence, wherein said control sequences are operably linked to said coding sequence.

The term "operably linked" as used herein refers to two or more components such as nucleic acid sequences or polypeptide sequences that are physically linked and are in a functional relationship with each other permitting them to function in their intended manner. For instance, a promoter is operably linked to a coding sequence if the promoter can regulate the transcription or expression of a coding sequence, in which case the coding sequence should be understood as being "under the control of" the promoter.

The term "parent polypeptide" refers to the polypeptide relative to which another polypeptide differs by substituting, adding or deleting one or more amino acids.

Position being defined with reference to SEQ ID NO: x means that the position in the amino acid sequence according to the disclosure at which a modification has taken place is given in respect with the position of the corresponding amino acid in the amino acid sequence according to SEQ ID NO: x when the two sequences are aligned using an alignment method as described herein.

The term "recombinant" when used in reference to a nucleic acid, or protein indicates that the nucleic acid, or protein has been modified in its sequence if compared to its native form by human intervention. The term "recombinant" when referring to a cell indicates that the genome of the cell has been modified in its sequence if compared to its native form by human intervention. The term "recombinant" is synonymous with "genetically modified".

A selectable marker is a gene which allows for selection of cells transformed with such a gene and which provides for biocide or viral resistance, resistance to heavy metals, prototrophy to auxotrophs, and the like.

Preferred selectable markers include, but are not limited to, those which confer resistance to drugs or which complement a defect in the cell. They include e. g. versatile marker genes that can be used for transformation of most filamentous fungi and yeasts such as acetamidase genes or cDNAs, or genes providing resistance to antibiotics.

Alternatively, specific selection markers can be used such as auxotrophic markers which require corresponding mutant strains. Preferably, the selection marker is deleted from the transformed cell after introduction of the expression construct so as to obtain transformed cells which are free of selection marker genes.

The term selectable marker extends to a marker gene used for screening, i.e. marker gene that, once introduced into a cell confers to the cell a visible phenotype and causes the cell look different. An example of marker for screening is a gene coding for a fluorescent protein which causes cells to fluoresce under an appropriate light source.

For the purpose of this disclosure, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this disclosure the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the disclosure is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present disclosure can further be used as a "query sequence" to perform a search against public databases to, for example, identify other family members or related sequences. Such searches can be performed using the BLASTN and BLASTX programs (version 2.0) of Altschul, et al. (1990) J. Mol. Biol. 215:403-10. BLAST nucleotide searches can be performed with the BLASTN program, score=100, wordlength=12 to obtain nucleotide sequences homologous to nucleic acid molecules of the disclosure. BLAST protein searches can be performed with the BLASTX program, score=50, wordlength=3 to obtain amino acid sequences homologous to protein molecules of the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTX and BLASTN) can be used. See the homepage of the National Center for Biotechnology Information at ncbi.nlm.nih.gov.

As used herein, the terms "variant," "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches. Variant polypeptides may differ from a reference polypeptide by a small number of amino acid residues and may be defined by their level of primary amino acid sequence homology/identity with a reference polypeptide. Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a reference polypeptide. Methods for determining percent identity are known in the art and described herein. Generally, the variants retain the characteristic nature of the reference polypeptide, but have altered properties in some specific aspects. For example, a variant may have a modified pH optimum, a modified substrate binding ability, a modified resistance to enzymatic degradation or other degradation, an increased or decreased activity, a modified temperature or oxidative stability, but retains its characteristic functionality. Variants further include polypeptides with chemical modifications that change the characteristics of a reference polypeptide.

With regard to nucleic acids, the terms refer to a nucleic acid that encodes a variant polypeptide, that has a specified degree of homology/identity with a reference nucleic acid, or that hybridizes under stringent conditions to a reference nucleic acid or the complement thereof. Preferably, a variant nucleic acid has at least 70%, at least 75%, at least 80%, at least 85%, at least 90%, at least 91%, at least 92%, at least 93%, at least 94%, at least 95%, at least 96%, at least 97%, at least 98%, or even at least 99% nucleic acid sequence identity with a reference nucleic acid. Methods for determining percent identity are known in the art and described herein.

The terms permease, facilitator, transporter or transport protein or related terms are all describing proteins with multiple membrane spanning domains that exhibit a function in transporting molecules across a membrane. This transport can be brought about by different mechanisms: uniport (transport of one molecule), symport (simultaneous co-transport of two different molecules in the same direction), antiport (simultaneous transport of two molecules in opposite directions), facilitated diffusion, group translocation (e.g. phosphotransferase systems) and primary transport (e.g. transport driven by hydrolysis of adenosine triphosphate or by light).

The family of sugar transporters in yeast can be divided in five clusters: hexose permeases (HXT-genes, GAL2), disaccharide permeases, myo-inositol permeases, sugar receptors and an additional cluster of transporters of which the substrate has been determined (Nelissen et al., 1997, FEMS Yeast Rev, 21, pp. 113-134).

In a first aspect, the invention provides a variant of a parent polypeptide which is preferably a hexose transporter, wherein the variant comprises an amino acid sequence which, when aligned with the amino acid sequence set out in SEQ ID NO: 1, comprises a substitution of amino acids N376 and T89, the positions of said amino acids being defined with reference to the amino acid sequence set out in SEQ ID NO: 1.

WO2014/195376 describes variants of hexose transporter polypeptides belonging to the Major Facilitator Superfamily (MFS), including Gal2 having substitutions at position N376 with increased preference towards xylose. However, WO2014/195376 is silent on the arabinose transport properties of N376 variants of Gal2 and does not disclose or suggest that substituting the threonine at position 89 to isoleucine results in a hexose transporter which has higher affinity for L-arabinose and which has lost all affinity for glucose (see Table 3).

The parent polypeptide is a member of the Major Facilitator Superfamily (MFS). Two main transporter families of which proteins are found throughout all living organism are the ATP-binding cassette (ABC) superfamily and the major facilitator superfamily (MFS), also known as the uniporter-symporter-antiporter family. Whereas ABC family permeases consist of multiple components and are primary active transporters, capable of transporting both small molecules and macromolecules only after generating energy through ATP hydrolysis, the MFS transporters consist of a single polypeptide of a secondary carrier which facilitates transport of small solutes in response to a chemiosmotic ion gradient. ABC superfamily and MFS proteins account for almost half of the solute transporters encoded within the microbial genomes (reviewed by Pao et al, 1998, Microbiol Mol Biol Rev.; 62 pp. 1-34, and Saier et al, 1999, J Mol Microbiol Biotechnol, 1 pp. 257-279).

The polypeptide according to SEQ ID NO: 1 is Gal2, which is a facilitated diffusion transporter. It belongs to the major facilitator superfamily, sugar transporter (TC 2.A.1.1) family. "Permease polypeptide", is also designated herein as "polypeptide permease" or "polypeptide". "Permease polypeptide polynucleotide", is herein a polynucleotide that encodes the permease polypeptide.

In an embodiment, the variant polypeptide has xylose transport activity and/or arabinose transport activity, and/or galactose transport activity.

The variant polypeptide of the invention may have one or more alternative and/or additional activities other than that of sugar permease activity.

As set out above, a variant polypeptide of the invention will typically have sugar permease activity. However, a variant polypeptide of the invention may have one or more of the activities set out above in addition to or alternative to that activity.

The variant polypeptide is not necessarily a polypeptide according to SEQ ID NO: 1. Rather, the variant polypeptide comprises substituted amino acids, which, in SEQ ID NO: 1, are at positions 89 and 376. However, in a hexose permease polypeptide having another amino acid sequence than SEQ ID NO: 1, such positions may have a different numbering, but still correspond to positions 89 or 376 of SEQ ID NO: 1.

Positions 89 and 376, for (other) hexose permease polypeptides can be identified by comparing 3D crystal structures, or by aligning the amino acid sequences, as explained inter alia in WO2014/195376, in particular on page 17, line 22 and onwards. For example, in hexose transporter polypeptide Hxt11 (SEQ ID NO: 10), position N376 of the polypeptide of SEQ ID NO: 1 corresponds to N366 and position T89 corresponds to T79.

In an embodiment, the variant polypeptide comprises the amino acid sequence set out in SEQ ID NO: 1.

In another embodiment, the substitution of amino acid N376 comprises any one of N376T, N376C, N376V, N376M, N376L, N376I, or N376F. That is, the variant polypeptide has an amino acid at position 376 which is a threonine, a cysteine, a valine, a methionine, a leucine, an isoleucine, or a phenylalanine. Preferably position 376 is T, S, or I.

In an embodiment, wherein the substitution of amino acid T89 comprises any one of T89I, T89V, T89L, T89S, T89M, or T89F.

That is, the variant polypeptide has an amino acid at position 89 which is an isoleucine, a valine, a leucine, a serine, a methionine, or a phenylalanine. Preferably, position 89 is an isoleucine.

In a preferred embodiment, the substitution of amino acid N376 comprises any one of N376T, N376S, or N376I, and the substitution of amino acid T89 comprises T89I.

In an embodiment, the variant polypeptide has at least 70% sequence identity with the amino acid sequence of the parent polypeptide or has at least 70% sequence identity of a polypeptide with an amino acid sequence corresponding to SEQ ID NO: 1. The variant may have at least 80% or 85% sequence identity with the amino acid sequence of the parent polypeptide or at least 80% or 85% sequence identity of a polypeptide with an amino acid sequence corresponding to SEQ ID NO: 1. The variant may have at least 90% sequence identity with the amino acid sequence of the parent polypeptide or at least 90% sequence identity of a polypeptide with an amino acid sequence corresponding to SEQ ID NO: 1. The variant may have at least 95% sequence identity with the amino acid sequence of the parent polypeptide or at least 95% sequence identity of a polypeptide with an amino acid sequence corresponding to SEQ ID NO: 1. The variant may have at least 98% sequence identity with the amino acid sequence of the parent polypeptide or at least 98% sequence identity of a polypeptide with an amino acid sequence corresponding to SEQ ID NO: 1. The variant may have at least 99% sequence identity with the amino acid sequence of the parent polypeptide or at least 99% sequence identity of a polypeptide with an amino acid sequence corresponding to SEQ ID NO: 1. The variant polypeptide is preferably a man-made polypeptide.

The invention further provides a nucleic acid sequence encoding the variant polypeptide of the invention, preferably wherein said nucleic acid sequence is man-made.

The invention also provides a nucleic acid construct comprising the nucleic acid sequence of the invention operably linked to one or more control sequences capable of directing the expression of the polypeptide variant in a suitable cell.

The invention also provides a recombinant expression cassette comprising the nucleic acid construct of the invention.

The invention also provides a recombinant yeast comprising the nucleic acid of the invention, the nucleic acid construct of the invention, and/or the expression cassette of the invention. The yeast is transformed with a nucleic acid sequence, a nucleic acid construct comprising said nucleic acid sequence, or a recombinant expression cassette comprising such nucleic acid construct. In an embodiment, such nucleic acid sequence encodes a variant polypeptide which is a mutant of a polypeptide that is native in the untransformed host cell. In an embodiment, the polypeptide that is native in the untransformed host cell is a transporter polypeptide chosen from the list consisting of Gal2, Hxt1, Hxt2, Hxt3, Hxt4, Hxt5, Hxt6, Hxt7, Hxt8, Hxt9, Hxt10, Hxt11, Hxt12, Hxt13, Hxt14, Hxt15, Hxt16 and Hxt17.

The recombinant yeast may be selected from *Saccharomycetaceae*, in particular from the group of *Saccharomyces*, such as *Saccharomyces cerevisiae; Kluyveromyces*, such as *Kluyveromyces marxianus; Pichia*, such as *Pichia/Scheffersomyces stipitis* or *Pichia angusta; Zygosaccharomyces*, such as *Zygosaccharomyces bailii*; and *Brettanomyces*, such as *Brettanomyces intermedius, Issatchenkia*, such as *Issatchenkia orientalis* and *Hansenula/Ogateae*.

The recombinant yeast may be subjected to evolutionary engineering to improve its properties. Evolutionary engineering processes are known processes. Evolutionary engineering is a process wherein industrially relevant phenotypes of a microorganism, herein the recombinant yeast, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5(2005) 925-934, WO2008/041840 and WO2009/112472. After the evolutionary engineering the resulting recombinant cell is isolated. The isolation may be executed in any known manner, e.g. by separation of cells from a recombinant cell broth used in the evolutionary engineering, for instance by taking a cell sample or by filtration or centrifugation.

In an embodiment, the recombinant yeast comprises one or more gene encoding an L-arabinose isomerase (E.C. 5.3.1.4; araA); one or more gene encoding an L-ribulokinase (E.C. 2.7.1.16; araB); and one or more gene encoding an L-ribulose-5-P4-epimerase (E.C. 5.1.3.4; araD); which genes allow said yeast to ferment arabinose. The genes for araA, araB and araD may be from *Lactobacillus plantarum*, as disclosed e.g. in WO2008/041840. Alternatively, an araA gene from *Bacillus subtilis* and araB and araD genes from *Escherichia coli* may be used as disclosed e.g. in EP1499708. Alternatively, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in e.g. WO2009/011591.

In an embodiment the recombinant yeast comprises a gene encoding an L-arabinose isomerase having an amino acid sequence according to SEQ ID NO: 5 or a functional homologue thereof having at least 60%, preferably at least 65%, at least 70%, at least 75%, at least 80%, at least 85%, at least 90%, at least 95%, at least 98%, at least 99% identity to SEQ ID NO: 5.

In an embodiment the recombinant yeast comprises a gene encoding an L-ribulokinase having an amino acid sequence according to SEQ ID NO: 6 or a functional homologue thereof having at least 60%, preferably at least 65%, at least 70%, at least 75%, at least 80%, at least 85%, at least 90%, at least 95%, at least 98%, at least 99% identity to SEQ ID NO: 6.

In an embodiment the recombinant yeast comprises a gene encoding an L-ribulose-5-P4-epimerase having an amino acid sequence according to SEQ ID NO: 7 or a functional homologue thereof having at least 60%, preferably at least 65%, at least 70%, at least 75%, at least 80%, at least 85%, at least 90%, at least 95%, at least 98%, at least 99% identity to SEQ ID NO: 7.

In one embodiment the recombinant yeast comprises one or more gene encoding a xylose isomerase (EC 5.3.1.5; such as xylA) and one or more gene encoding a xylulose kinase (E.C. 2.7.1.17; such as XKS1); or one or more gene encoding a xylose reductase (E.C. 1.1.1.307; such as XYL1 from *Pichia/Scheffersomyces stipitis*) and one or more genes encoding a xylitol dehydrogenase (E.C. 1.1.1.B19; such as XYL2 from *Scheffersomyces stipitis*) to allow the recombinant yeast to ferment xylose.

In an embodiment the recombinant yeast comprises a gene encoding a xylose isomerase having an amino acid sequence according to SEQ ID NO: 8 or a functional homologue thereof having at least 60%, preferably at least 65%, at least 70%, at least 75%, at least 80%, at least 85%, at least 90%, at least 95%, at least 98%, at least 99% identity to SEQ ID NO: 8.

In an embodiment the recombinant yeast comprises a gene encoding a xylulose kinase having an amino acid sequence according to SEQ ID NO: 9 or a functional homologue thereof having at least 60%, preferably at least 65%, at least 70%, at least 75%, at least 80%, at least 85%, at least 90%, at least 95%, at least 98%, at least 99% identity to SEQ ID NO: 9.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor. Assays to measure activity of xylose isomerase and xylulose kinase are described inter alia in WO2003/062430.

In an embodiment the recombinant yeast further comprises overexpression of one or more genes of the non-oxidative branch of the pentose phosphate pathway.

In an embodiment the one or more genes of the pentose phosphate pathway that is overexpressed encodes for an enzyme selected from the list of a transaldolase (EC 2.2.1.2), a transketolase (EC 2.2.1.1), a ribose-5-phosphate isomerase (EC 5.3.1.6) and a D-ribulose-5-phosphate 3-epimerase (EC 5.1.3.1).

In another embodiment the one or more genes of the pentose phosphate pathway that is overexpressed is selected from the list of TAL1, TAL2, NQM1, TKL1, TKL2, RPE1 and RKI1.

The invention also provides a method of designing a variant sequence of a parent polypeptide sequence, which method comprises:
a) selecting a parent polypeptide sequence, preferably a parent polypeptide with an amino acid sequence according to SEQ ID NO: 1;
b) substituting in said polypeptide sequence amino acids N376 and T89, the position of said amino acids being defined with reference to SEQ ID NO: 1.

In an embodiment, in step b) the substitutions of amino acids N376 result in any one of N376T, N376C, N376V, N376M, N376L, N376I, or N376F and the substitution of amino acid T89 results in any one of T89I, T89V, T89L, T89S, T89M, or T89F.

Preferably, the substitution of amino acid N376 results in any one of N376T, N376S, or N376I and the substitution of amino acid T89 results in T89I.

Techniques to design nucleic acids constructs encoding variant polypeptides, recombination expression cassettes, to transform yeast cells therewith, are described inter alia in WO2014/195376

The invention also provides a process for the production of a fermentation product, preferably ethanol comprising:
fermenting a composition comprising a lignocellulosic biomass, in particular comprising glucose and arabinose, preferably also comprising galactose, under anaerobic conditions in the presence of a recombinant yeast according to the invention; and
recovering the fermentation product.

The fermentation product may be any of ethanol, butanol, lactic acid, di-terpene, glycosylated di-terpene, 3-hydroxy-propionic acid, acrylic acid, acetic acid, succinic acid, citric acid, fumaric acid, malic acid, itaconic acid, an amino acid, 1,3-propane-diol, ethylene, glycerol, a ß-lactam antibiotic or a cephalosporin. Ethanol is a preferred fermentation product.

Anaerobic conditions are herein defined as conditions without any oxygen or in which essentially no oxygen is consumed by the recombinant yeast and usually corresponds to an oxygen consumption of less than 5 mmol/l·h, in particular to an oxygen consumption of less than 2.5 mmol/l·h, or less than 1 mmol/l·h. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation. The process can also be carried out under micro-aerobic conditions.

In an embodiment the lignocellulosic biomass comprises lignocellulose and/or hemicellulose. The composition may be a biomass hydrolysate. Such biomass hydrolysate may be a lignocellulosic biomass hydrolysate. Lignocellulose herein includes hemicellulose and hemicellulose parts of biomass. Lignocellulose may also include lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert.

The lignocellulosic biomass may comprise pectin and/or other pectic substances such as arabinans, which may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

In another embodiment such composition is a pre-treated cornstover hydrolysate. Another preferred composition is a corn fiber hydrolysate, which is optionally pre-treated.

The composition preferably comprises glucose and arabinose, preferably also galactose. In an embodiment at least some of the glucose and at least some of the arabinose is consumed, preferably at least some of the glucose and at least some of the arabinose and at least some of the galactose is consumed.

The invention also provides the use of the recombinant yeast cell of the invention for the production of a fermentation product, preferably ethanol, from a composition comprising glucose, arabinose, and preferably also comprising galactose.

Example

Materials and Methods

Strains and Maintenance

The construction of hexose transporter deletion *S. cerevisiae* strain DS68625 used for sugar uptake experiments in the example below was previously described in Shin et al., 2015 (An engineered cryptic Hxt11 sugar transporter facilitates glucose-xylose co-consumption in *Saccharomyces cerevisiae*, Biotechnology for Biofuels, volume 8, p. 176). The genotype of DS68625 is described as:

Mat a, ura3-52, leu2-112, gre3::loxP, loxP-Ptpi:TAL1, loxP-Ptpi::RKI1, loxP-Ptpi-TKL1, loxP-Ptpi-RPE1, delta::Padh1XKS1Tcyc1-LEU2, delta::URA3-Ptpi-xylA-Tcyc1, his3::loxP, hxt2::loxP-kanMX-loxP, hxt367::loxP-hphMX-loxP, hxt145::loxP-natMX-loxP, gal2::loxP-zeoMX-loxP Stock cultures were grown in shake flasks on yeast-extract/peptone (YP) medium (10 g/L Bacto yeast extract, Becton Dickinson, Franklin Lakes, N.J., and 20 g/L Bacto Peptone, Becton Dickinson), This media was supplemented with 20 g/L maltose. Frozen stock cultures were prepared by adding glycerol (30% vol/vol) to stock cultures, after which 1 mL aliquots were stored at −80° C.

Cultivation and Media

Strain characterisation studies were performed in synthetic medium (SM) prepared as described previously (Verduyn C, Postma E, Scheffers W A, Van Dijken J P: Effect of benzoic acid on metabolic fluxes in yeasts: a continuous-culture study on the regulation of respiration and alcoholic fermentation. Yeast 1992, 8:501-517). Carbon source and vitamin solutions were added after autoclaving the medium for 20 min at 121° C. 50% w/v D-xylose solution was autoclaved separately at 110° C. for 20 min. Prior to inoculation 20 g/L D-xylose (SMX) or 20 g/L maltose (SMM) was added to SM as carbon source. SMX medium was used to propagate DS68625 derived transformants for sugar uptake assays. SMM medium was used in plates for selection after transformation.

Aerobic shake-flask cultures were grown in an orbital shaker at 200 rpm set at 30° C., using 500-ml flasks containing 100 ml medium. For plates 20 g/L agar (BD) was added prior to autoclaving at 121° C. for 20 min.

Plasmid and Strain Construction

The protein sequence for Gal2 originating from CEN.PK113-7D is given as SEQ ID NO: 1. The coding DNA sequence for GAL2 (YLR081W) found in CEN.PK113-7D is given as SEQ ID NO: 2 SEQ ID NO: 2 can be synthesized artificially at a DNA synthesis company and can be used as template for site-directed mutagenesis to generate specific Gal2 variants. The Gal2 variants tested in example below are given in Table 1.

TABLE 1

Amino acid changes in Gal2 variants

| Variant | Amino acid at position 89 | Amino acid at position 376 |
| --- | --- | --- |
| Gal2 (wt) | T | N |
| Gal2$^{N376I}$ | T | I |
| Gal2$^{N376S}$ | T | S |
| Gal2$^{N376T}$ | T | T |
| Gal2$^{N376T, T89I}$ | I | T |
| Gal2$^{T89I}$ | I | N |

Plasmids constructed and used in this study are shown in Table 2. Plasmid DNA was isolated from *E. coli* cultures using a GenElute Plasmid kit (Sigma-Aldrich, St. Louis, Mo.). PCR amplification of expression cassettes and plasmid fragments was performed using Phusion High Fidelity DNA Polymerase (Thermo Scientific, Waltham, Mass., USA).

TABLE 2

GAL2 Expression plasmids

| Plasmid | Characteristic | Source |
| --- | --- | --- |
| pRS313-mcs | CEN6/ARS4 HIS3 ampR pHXT7-mcs-tHXT7 | Nijland et al., 2014* |
| pRS313-Gal2 | CEN6/ARS4 HIS3 ampR pHXT7-GAL2-tHXT7 | This example |
| pRS313-Gal2-TT | CEN6/ARS4 HIS3 ampR pHXT7-GAL2$^{N376T}$-tHXT7 | This example |
| pRS313-Gal2-ST | CEN6/ARS4 HIS3 ampR pHXT7-GAL2$^{N376S}$-tHXT7 | This example |
| pRS313-Gal2-IT | CEN6/ARS4 HIS3 ampR pHXT7-GAL2$^{N376I}$-tHXT7 | This example |
| pRS313-Gal2-TI | CEN6/ARS4 HIS3 ampR pHXT7-GAL2$^{N376T/T89I}$-tHXT7 | This example |
| pRS313-Gal2-NI | CEN6/ARS4 HIS3 ampR pHXT7-GAL2$^{T89I}$-tHXT7 | This example |

*Nijland J G, Shin H Y, de Jong R M, De Waal P P, Klaassen P, Driessen A J: Engineering of an endogenous hexose transporter into a specific D-xylose transporter facilitates glucose-xylose co-consumption in *Saccharomyces cerevisiae*. Biotechnol Biofuels 2014, 7: 168.

To construct expression plasmids, wildtype GAL2 and the abovementioned GAL2 variants were used as template and amplified using the primers F_Gal2_XbaI (SEQ ID NO: 3) and R_Gal2_Cfr9I (SEQ ID NO: 4). Resulting PCR fragments were subsequently cloned into plasmid pRS313-P7T7 similarly as described in Nijland et al., 2014 (Biotechnology for Biofuels, vol. 7, p. 168). All genes were cloned into pRS313-P7T7 and subsequently confirmed by Sanger sequencing (Baseclear, Leiden, The Netherlands).

*S. cerevisiae* strains were transformed as described by Gietz and Woods (Gietz R D, Schiestl R H, Willems A R, Woods R A: Studies on the transformation of intact yeast cells by the LiAc/SS-DNA/PEG procedure. Yeast 1995, 11). The Gal2 variants and the pRS313-P7T7-mcs plasmid (as an empty plasmid/control) were transformed to the hexose transporter deletion strain DS68625. Transformants were selected on SMM agar plates based on complementation by the GAL2 expression plasmids (which bear the HIS3 marker) of the histidine auxotrophy of DS68625. Resulting positive colonies were selected for each construct and named DS68625-Gal2, DS68625-Gal2 N376I, DS68625-Gal2 N376S, DS68625-Gal2 N376T, DS68625-Gal2 N376T/T89I, DS68625-Gal2 T89I and DS68625-mcs.

Sugar Transport Assays

Strains were pre-grown in aerobic shake flasks on SMX after which cells were collected by centrifugation (3000 g, 3 min), washed and re-suspended in SM without sugar. Uptake experiments were initiated by adding [$^{14}$C] L-arabinose or [$^{14}$C] D-glucose (ARC St. Louis, Mo., USA) to the cell suspension with varying concentrations between 0.2 and 500 mM. [$^{14}$C] L-arabinose and [$^{14}$C] D-glucose were added 50-60 mCi/mmol at a concentration of 0.1 mCi/ml and labelled at the first carbon atom. At set time points, uptake was arrested by adding 5 mL of ice-cold 0.1 M LiCl, filtration over 0.45-μm HV membrane filters (Millipore, France) and washing with 5 mL ice-cold 0.1 M LiCl. Radioactivity on the filters was then counted using a Liquid Scintillation Counter (PerkinElmer, Waltham, Mass., USA) in Ultima Gold MV Scintillation cocktail (PerkinElmer, Waltham, Mass., USA). D-Glucose inhibition experiments were measured using 50 mM [$^{14}$C] L-arabinose with [$^{14}$C] D-glucose added at concentrations between 50 and 500 mM.

Results

The inhibitory effect of D-glucose on L-arabinose transport of positions N376 and T89 was tested in in S. cerevisiae DS68625. To examine the extent to which D-glucose inhibited L-arabinose uptake, [$^{14}$C]-L-arabinose-uptake experiments were performed at different concentrations of D-glucose (FIG. 1). L-arabinose uptake by wild-type Gal2 was severely inhibited by D-glucose. The Gal2$^{N376T}$ and Gal2$^{N376T/T89I}$ substitutions significantly decreased inhibition of L-arabinose uptake by D-glucose, while D-glucose inhibition was not significantly affected by only the Gal2$^{T89I}$ substitution (FIG. 1).

In transport assays with [$^{14}$C]-L-arabinose or [$^{14}$C]-D-glucose, Gal2$^{N376I}$, Gal2$^{N376S}$ and Gal2$^{N376T}$ substitutions yielded lower $K_m$ values for L-arabinose than wild-type Gal2, while their $K_m$ values for D-glucose were one to two orders of magnitude higher than those of wild-type Gal2. As a result, the ratios of the $K_m$ values for L-arabinose vs. D-glucose was 2 orders of magnitude lower for the strains expression Gal2 variants with substitutions at position 376. For Gal2 variants that only carried an amino acid substitution at this position, transport capacities ($V_{max}$) for L-arabinose and D-glucose differed by less than two-fold from those of wild-type Gal2 (Table 3). These changes in transport kinetics are consistent with a strongly reduced competitive inhibition of L-arabinose transport by D-glucose. A single Gal2$^{T89I}$ substitution only slightly increased the $K_m$ for D-glucose transport, while it decreased the $K_m$ for L-arabinose 335 to 99 mM. For both sugars, the Gal2$^{T89I}$ substitution caused a 2-3 fold reduction of $V_{max}$ (Table 3). These kinetic properties suggest that Gal2$^{T89I}$ may, by itself, confer a selective advantage at lower extracellular L-arabinose concentrations. Remarkably, a Gal2 variant that harboured both the Gal2$^{N376T}$ and Gal2$^{T89I}$ substitutions did no longer transport D-glucose, while $K_m$ and $V_{max}$ for L-arabinose were similar to those of Gal2$^{T89I}$ (Table 3).

TABLE 3

$K_m$ and $V_{max}$ values for L-arabinose and D-glucose for Gal2 variants with amino acid substitutions at position N376 and T89. Transport kinetics were measured by uptake studies with radioactive sugars after expression of GAL2 alleles in S. cerevisiae DS68625. Values are average and mean deviation of two independent sets of uptake experiments. Data used to calculate $K_m$ and $V_{max}$ values are shown in FIG. 3A-3D.

| | Km (mM) | | Km ratio | Vmax (nmol (mg biomass)/min | |
|---|---|---|---|---|---|
| Gal2 variant | L-arabinose | D-glucose | Ara/Glc | L-arabinose | D-glucose |
| Gal2$^1$ | 335 ± 21 | 1.9 ± 0.2 | 176 | 75 ± 5 | 26 ± 1 |
| Gal2$^{N376I}$ | 117 ± 16 | 101 ± 47 | 1 | 39 ± 3 | 32 ± 18 |
| Gal2$^{N376S}$ | 186 ± 33 | 38 ± 1 | 5 | 64 ± 2 | 28 ± 1 |
| Gal2$^{N376T}$ | 171 ± 17 | 57 ± 1 | 3 | 65 ± 2 | 17 ± 4 |
| Gal2$^{T89I+N376T}$ | 103 ± 40 | — | — | 30 ± 2 | *) |
| Gal2$^{T89I}$ | 99 ± 18 | 7 ± 0.2 | 15 | 22 ± 3 | 13 ± 0.1 |

*) The detection limit for determining the d-glucose uptake velocity Vmax is 1.8 nmol$^{-1}$ (mg biomass)$^{-1}$ min$^{-1}$.

The invention claimed is:

1. A nucleic acid sequence encoding a variant of a parent polypeptide which is optionally a hexose transporter, wherein the parent polypeptide comprises the amino acid sequence of SEQ ID NO:1, and wherein the variant comprises an amino acid sequence which, when aligned with the amino acid sequence of SEQ ID NO:1, comprises a substitution of amino acids N376 and T89, the positions of said amino acids being defined with reference to the amino acid sequence of SEQ ID NO:1, wherein the substitution of amino acid T89 comprises any one of T89I, T89V, T89S, T89M, or T89F.

2. A nucleic acid construct comprising the nucleic acid sequence of claim 1 operably linked to one or more control sequences capable of directing expression of the variant in a suitable cell.

3. A recombinant expression cassette comprising the nucleic acid construct of claim 2.

4. A recombinant yeast comprising the nucleic acid sequence of claim 1, a nucleic acid construct comprising the nucleic acid sequence, and/or an expression cassette comprising said construct.

5. The recombinant yeast according to claim 4 further comprising one or more genes encoding an L-arabinose isomerase (E.C. 5.3.1.4; araA); one or more genes encoding an L-ribulokinase (E.C. 2.7.1.16; araB); and one or more genes encoding an L-ribulose-5-P-4-epimerase (E.C. 5.1.3.4; araD).

6. The recombinant yeast according to claim 4 further comprising one or more gene encoding a xylose isomerase (EC 5.3.1.5) optionally xylA and one or more gene encoding a xylulose kinase (E.C. 2.7.1.17) optionally XKS1.

7. The recombinant yeast according to claim 4 further comprising overexpression of one or more genes of a non-oxidative branch of a pentose phosphate pathway.

8. The recombinant yeast according to claim 7 wherein one or more genes of the pentose phosphate pathway that is overexpressed encodes an enzyme selected from a transaldolase (EC 2.2.1.2), a transketolase (EC 2.2.1.1), a ribose-5-phosphate isomerase (EC 5.3.1.6) and a D-ribulose-5-phosphate 3-epimerase (EC 5.1.3.1).

9. The recombinant yeast according to claim 7 wherein one or more genes of the pentose phosphate pathway that is overexpressed is selected from TAL1, NQM1, TKL1, TKL2, RPE1 and RKI1.

10. A process for the production of ethanol comprising:
fermenting a composition comprising a lignocellulosic biomass, optionally comprising glucose and arabinose, optionally also comprising galactose, under anaerobic conditions in the presence of the recombinant yeast according to claim 4; and
recovering the ethanol.

11. The process according to claim 10 wherein the lignocellulosic biomass comprises lignocellulose and/or hemicellulose and/or pectin.

12. The nucleic acid sequence of claim 1, wherein the substitution of amino acid N376 comprises any one of N376T, N376C, N376V, N376M, N376L, N376I, or N376F.

13. The nucleic acid sequence of claim 1, wherein the substitution of amino acid N376 comprises any one of N376T, N376S, or N376I, and wherein the substitution of amino acid T89 comprises T89I.

14. The nucleic acid sequence of claim 1, wherein the variant has at least 80% sequence identity with the amino acid sequence of the parent polypeptide.

* * * * *

SEQUENCE LISTING

```
<160> NUMBER OF SEQ ID NOS: 10

<210> SEQ ID NO 1
<211> LENGTH: 574
<212> TYPE: PRT
<213> ORGANISM: Saccharomyces cerevisiae
<220> FEATURE:
<221> NAME/KEY: MISC_FEATURE
<222> LOCATION: (1)..(574)
<223> OTHER INFORMATION: S. cerevisiae WT Gal2p amino acid sequence
      CEN.PK113-7D
```

```
<400> SEQUENCE: 1

Met Ala Val Glu Glu Asn Asn Met Pro Val Ser Gln Gln Pro Gln
1               5                   10                  15

Ala Gly Glu Asp Val Ile Ser Ser Leu Ser Lys Asp Ser His Leu Ser
                20                  25                  30

Ala Gln Ser Gln Lys Tyr Ser Asn Asp Glu Leu Lys Ala Gly Glu Ser
            35                  40                  45

Gly Pro Glu Gly Ser Gln Ser Val Pro Ile Glu Ile Pro Lys Lys Pro
        50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
                100                 105                 110

Thr His Tyr Leu Ser Asn Val Arg Thr Gly Leu Ile Val Ala Ile Phe
            115                 120                 125

Asn Ile Gly Cys Ala Phe Gly Gly Ile Ile Leu Ser Lys Gly Gly Asp
130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
                180                 185                 190

Leu Cys Pro Met Leu Ile Ser Glu Ile Ala Pro Lys His Leu Arg Gly
            195                 200                 205

Thr Leu Val Ser Cys Tyr Gln Leu Met Ile Thr Ala Gly Ile Phe Leu
210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
            275                 280                 285

Ser Pro Glu Asp Pro Ala Val Gln Ala Glu Leu Asp Leu Ile Met Ala
        290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
                340                 345                 350

Gly Thr Val Ile Phe Lys Ser Val Gly Leu Asp Asp Ser Phe Glu Thr
            355                 360                 365

Ser Ile Val Ile Gly Val Val Asn Phe Ala Ser Thr Phe Phe Ser Leu
        370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
```

```
            405                 410                 415
Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
            435                 440                 445

Thr Trp Ala Pro Val Ala Trp Val Ile Thr Ala Glu Ser Phe Pro Leu
            450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
                500                 505                 510

Phe Tyr Val Phe Phe Phe Val Pro Glu Thr Lys Gly Leu Ser Leu Glu
            515                 520                 525

Glu Ile Gln Glu Leu Trp Glu Glu Gly Val Leu Pro Trp Lys Ser Glu
            530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570
```

<210> SEQ ID NO 2
<211> LENGTH: 1725
<212> TYPE: DNA
<213> ORGANISM: Saccharomyces cerevisiae
<220> FEATURE:
<221> NAME/KEY: misc_feature
<222> LOCATION: (1)..(1725)
<223> OTHER INFORMATION: S. cerevisiae GAL2 gene nucleic acid sequence
      CEN.PK113-7D

<400> SEQUENCE: 2

```
atggcagttg aggagaacaa tatgcctgtt gtttcacagc aaccccaagc tggtgaagac      60
gtgatctctt cactcagtaa agattcccat ttaagcgcac aatctcaaaa gtattccaat     120
gatgaattga aagccggtga gtcagggcct gaaggctccc aaagtgttcc tatagagata     180
cccaagaagc ccatgtctga atatgttacc gtttccttgc tttgtttgtg tgttgccttc     240
ggcggcttca tgtttggctg ggataccggt actatttctg gtttgttgt ccaaacagac     300
tttttgagaa ggtttggtat gaaacataag gatggtaccc actatttgtc aaacgtcaga     360
acaggtttaa tcgtcgccat tttcaatatt ggctgtgcct tggtggtat tatactttcc     420
aaaggtggag atatgtatgg ccgtaaaaag ggtctttcga ttgtcgtctc ggtttatata     480
gttggtatta tcattcaaat tgcctctatc aacaagtggt accaatattt cattggtaga     540
atcatatctg gtttgggtgt cggcggcatc gccgtcttat gtcctatgtt gatctctgaa     600
attgctccaa agcacttgag aggcacacta gtttcttgtt atcagctgat gattactgca     660
ggtatctttt tgggctactg tactaattac ggtacaaaga gctattcgaa ctcagttcaa     720
tggagagttc cattagggct atgtttcgct tggtcattat ttatgattgg cgcttttgacg     780
ttagttcctg aatccccacg ttatttatgt gaggtgaata ggtagaaga cgccaagctt     840
tccattgcta agtctaacaa ggtgtcacca gaggatcctg ccgtccaggc agagttagat     900
ctgatcatgg ccgtatagaa gctgaaaaaa ctggctggca atgcgtcctg ggggaatta     960
ttttccacca agaccaaagt atttcaacgt tgttgatgg gtgtatttgt tcaaatgttc    1020
```

```
caacaattaa ccggtaacaa ttattttttc tactacggta ccgttatttt caagtcagtt    1080
ggcctggatg attcctttga acatccatt  gtcattggtg tagtcaactt tgcctccact    1140
ttctttagtt tgtggactgt cgaaaacttg gggcgtcgta atgtttact  tttgggcgct    1200 gccactatga tggcttgtat ggtcatctac gcctctgttg gtgttaccag attatatcct    1260
cacggtaaaa gccagccatc ttctaaaggt gccggtaact gtatgattgt ctttacctgt    1320
ttttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcaccca  ttcatcacat ctgccattaa cttctactac    1500
ggttatgtct tcatgggctg tttggttgcc atgttttttt atgtcttttt ctttgttcca    1560
gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa                    1725
```

<210> SEQ ID NO 3
<211> LENGTH: 35
<212> TYPE: DNA
<213> ORGANISM: Artificial Sequence
<220> FEATURE:
<223> OTHER INFORMATION: F Gal2 XbaI

<400> SEQUENCE: 3

```
actcgtctag aatggcagtt gaggagaaca atatg                                  35
```

<210> SEQ ID NO 4
<211> LENGTH: 34
<212> TYPE: DNA
<213> ORGANISM: Artificial Sequence
<220> FEATURE:
<223> OTHER INFORMATION: R Gal2 Cfr9I

<400> SEQUENCE: 4

```
gcagcccggg ttatacgact tcttcgtgag tggc                                   34
```

<210> SEQ ID NO 5
<211> LENGTH: 474
<212> TYPE: PRT
<213> ORGANISM: Lactobacillus plantarum
<220> FEATURE:
<221> NAME/KEY: MISC_FEATURE
<222> LOCATION: (1)..(474)
<223> OTHER INFORMATION: L. plantarum L-arabinose isomerase (araA)

<400> SEQUENCE: 5

```
Met Leu Ser Val Pro Asp Tyr Glu Phe Trp Phe Val Thr Gly Ser Gln
1               5                   10                  15

His Leu Tyr Gly Glu Glu Gln Leu Lys Ser Val Ala Lys Asp Ala Gln
            20                  25                  30

Asp Ile Ala Asp Lys Leu Asn Ala Ser Gly Lys Leu Pro Tyr Lys Val
        35                  40                  45

Val Phe Lys Asp Val Met Thr Thr Ala Glu Ser Ile Thr Asn Phe Met
    50                  55                  60

Lys Glu Val Asn Tyr Asn Asp Lys Val Ala Gly Val Ile Thr Trp Met
65                  70                  75                  80

His Thr Phe Ser Pro Ala Lys Asn Trp Ile Arg Gly Thr Glu Leu Leu
                85                  90                  95

Gln Lys Pro Leu Leu His Leu Ala Thr Gln Tyr Leu Asn Asn Ile Pro
```

100                 105                 110
Tyr Ala Asp Ile Asp Phe Asp Tyr Met Asn Leu Asn Gln Ser Ala His
                115                 120                 125
Gly Asp Arg Glu Tyr Ala Tyr Ile Asn Ala Arg Leu Gln Lys His Asn
            130                 135                 140
Lys Ile Val Tyr Gly Tyr Trp Gly Asp Glu Asp Val Gln Glu Gln Ile
145                 150                 155                 160
Ala Arg Trp Glu Asp Val Ala Val Ala Tyr Asn Glu Ser Phe Lys Val
                165                 170                 175
Lys Val Ala Arg Phe Gly Asp Thr Met Arg Asn Val Ala Val Thr Glu
            180                 185                 190
Gly Asp Lys Val Glu Ala Gln Ile Lys Met Gly Trp Thr Val Asp Tyr
            195                 200                 205
Tyr Gly Ile Gly Asp Leu Val Glu Glu Ile Asn Lys Val Ser Asp Ala
            210                 215                 220
Asp Val Asp Lys Glu Tyr Ala Asp Leu Glu Ser Arg Tyr Glu Met Val
225                 230                 235                 240
Gln Gly Asp Asn Asp Ala Asp Thr Tyr Lys His Ser Val Arg Val Gln
                245                 250                 255
Leu Ala Gln Tyr Leu Gly Ile Lys Arg Phe Leu Glu Arg Gly Gly Tyr
            260                 265                 270
Thr Ala Phe Thr Thr Asn Phe Glu Asp Leu Trp Gly Met Glu Gln Leu
            275                 280                 285
Pro Gly Leu Ala Ser Gln Leu Leu Ile Arg Asp Gly Tyr Gly Phe Gly
            290                 295                 300
Ala Glu Gly Asp Trp Lys Thr Ala Ala Leu Gly Arg Val Met Lys Ile
305                 310                 315                 320
Met Ser His Asn Lys Gln Thr Ala Phe Met Glu Asp Tyr Thr Leu Asp
                325                 330                 335
Leu Arg His Gly His Glu Ala Ile Leu Gly Ser His Met Leu Glu Val
            340                 345                 350
Asp Pro Ser Ile Ala Ser Asp Lys Pro Arg Val Glu Val His Pro Leu
            355                 360                 365
Asp Ile Gly Gly Lys Asp Asp Pro Ala Arg Leu Val Phe Thr Gly Ser
            370                 375                 380
Glu Gly Glu Ala Ile Asp Val Thr Val Ala Asp Phe Arg Asp Gly Phe
385                 390                 395                 400
Lys Met Ile Ser Tyr Ala Val Asp Ala Asn Lys Pro Glu Ala Glu Thr
                405                 410                 415
Pro Asn Leu Pro Val Ala Lys Gln Leu Trp Thr Pro Lys Met Gly Leu
            420                 425                 430
Lys Lys Gly Ala Leu Glu Trp Met Gln Ala Gly Gly His His Thr
            435                 440                 445
Met Leu Ser Phe Ser Leu Thr Glu Glu Gln Met Glu Asp Tyr Ala Thr
            450                 455                 460
Met Val Gly Met Thr Lys Ala Phe Leu Lys
465                 470

<210> SEQ ID NO 6
<211> LENGTH: 533
<212> TYPE: PRT
<213> ORGANISM: Lactobacillus plantarum
<220> FEATURE:
<221> NAME/KEY: MISC_FEATURE
<222> LOCATION: (1)..(533)

<223> OTHER INFORMATION: L. plantarum L-ribulokinase (araB)

<400> SEQUENCE: 6

```
Met Asn Leu Val Glu Thr Ala Gln Ala Ile Lys Thr Gly Lys Val Ser
1               5                   10                  15

Leu Gly Ile Glu Leu Gly Ser Thr Arg Ile Lys Ala Val Leu Ile Thr
            20                  25                  30

Asp Asp Phe Asn Thr Ile Ala Ser Gly Ser Tyr Val Trp Glu Asn Gln
        35                  40                  45

Phe Val Asp Gly Thr Trp Thr Tyr Ala Leu Glu Asp Val Trp Thr Gly
    50                  55                  60

Ile Gln Gln Ser Tyr Thr Gln Leu Ala Ala Asp Val Arg Ser Lys Tyr
65                  70                  75                  80

His Met Ser Leu Lys His Ile Asn Ala Ile Gly Ile Ser Ala Met Met
                85                  90                  95

His Gly Tyr Leu Ala Phe Asp Gln Gln Ala Lys Leu Leu Val Pro Phe
            100                 105                 110

Arg Thr Trp Arg Asn Asn Ile Thr Gly Gln Ala Ala Asp Glu Leu Thr
        115                 120                 125

Glu Leu Phe Asp Phe Asn Ile Pro Gln Arg Trp Ser Ile Ala His Leu
    130                 135                 140

Tyr Gln Ala Ile Leu Asn Asn Glu Ala His Val Lys Gln Val Asp Phe
145                 150                 155                 160

Ile Thr Thr Leu Ala Gly Tyr Val Thr Trp Lys Leu Ser Gly Glu Lys
                165                 170                 175

Val Leu Gly Ile Gly Asp Ala Ser Gly Val Phe Pro Ile Asp Glu Thr
            180                 185                 190

Thr Asp Thr Tyr Asn Gln Thr Met Leu Thr Lys Phe Ser Gln Leu Asp
        195                 200                 205

Lys Val Lys Pro Tyr Ser Trp Asp Ile Arg His Ile Leu Pro Arg Val
    210                 215                 220

Leu Pro Ala Gly Ala Ile Ala Gly Lys Leu Thr Ala Ala Gly Ala Ser
225                 230                 235                 240

Leu Leu Asp Gln Ser Gly Thr Leu Asp Ala Gly Ser Val Ile Ala Pro
                245                 250                 255

Pro Glu Gly Asp Ala Gly Thr Gly Met Val Gly Thr Asn Ser Val Arg
            260                 265                 270

Lys Arg Thr Gly Asn Ile Ser Val Gly Thr Ser Ala Phe Ser Met Asn
        275                 280                 285

Val Leu Asp Lys Pro Leu Ser Lys Val Tyr Arg Asp Ile Asp Ile Val
    290                 295                 300

Met Thr Pro Asp Gly Ser Pro Val Ala Met Val His Val Asn Asn Cys
305                 310                 315                 320

Ser Ser Asp Ile Asn Ala Trp Ala Thr Ile Phe His Glu Phe Ala Ala
                325                 330                 335

Arg Leu Gly Met Glu Leu Lys Pro Asp Arg Leu Tyr Glu Thr Leu Phe
            340                 345                 350

Leu Glu Ser Thr Arg Ala Asp Ala Asp Ala Gly Gly Leu Ala Asn Tyr
        355                 360                 365

Ser Tyr Gln Ser Gly Glu Asn Ile Thr Lys Ile Gln Ala Gly Arg Pro
    370                 375                 380

Leu Phe Val Arg Thr Pro Asn Ser Lys Phe Ser Leu Pro Asn Phe Met
385                 390                 395                 400
```

```
Leu Thr Gln Leu Tyr Ala Ala Phe Ala Pro Leu Gln Leu Gly Met Asp
                405                 410                 415

Ile Leu Val Asn Glu Glu His Val Gln Thr Asp Val Met Ile Ala Gln
            420                 425                 430

Gly Gly Leu Phe Arg Thr Pro Val Ile Gly Gln Gln Val Leu Ala Asn
        435                 440                 445

Ala Leu Asn Ile Pro Ile Thr Val Met Ser Thr Ala Gly Glu Gly Gly
    450                 455                 460

Pro Trp Gly Met Ala Val Leu Ala Asn Phe Ala Cys Arg Gln Thr Ala
465                 470                 475                 480

Met Asn Leu Glu Asp Phe Leu Asp Gln Glu Val Phe Lys Glu Pro Glu
                485                 490                 495

Ser Met Thr Leu Ser Pro Glu Pro Glu Arg Val Ala Gly Tyr Arg Glu
            500                 505                 510

Phe Ile Gln Arg Tyr Gln Ala Gly Leu Pro Val Glu Ala Ala Ala Gly
        515                 520                 525

Gln Ala Ile Lys Tyr
        530

<210> SEQ ID NO 7
<211> LENGTH: 242
<212> TYPE: PRT
<213> ORGANISM: Lactobacillus plantarum
<220> FEATURE:
<221> NAME/KEY: MISC_FEATURE
<222> LOCATION: (1)..(242)
<223> OTHER INFORMATION: L. plantarum L-ribulose-5-P4-epimerase (araD)

<400> SEQUENCE: 7

Met Leu Glu Ala Leu Lys Gln Glu Val Tyr Glu Ala Asn Met Gln Leu
1               5                   10                  15

Pro Lys Leu Gly Leu Val Thr Phe Thr Trp Gly Asn Val Ser Gly Ile
            20                  25                  30

Asp Arg Glu Lys Gly Leu Phe Val Ile Lys Pro Ser Gly Val Asp Tyr
        35                  40                  45

Gly Glu Leu Lys Pro Ser Asp Leu Val Val Asn Leu Gln Gly Glu
    50                  55                  60

Val Val Glu Gly Lys Leu Asn Pro Ser Ser Asp Thr Pro Thr His Thr
65                  70                  75                  80

Val Leu Tyr Asn Ala Phe Pro Asn Ile Gly Gly Ile Val His Thr His
                85                  90                  95

Ser Pro Trp Ala Val Ala Tyr Ala Ala Ala Gln Met Asp Val Pro Ala
            100                 105                 110

Met Asn Thr Thr His Ala Asp Thr Phe Tyr Gly Asp Val Pro Ala Ala
        115                 120                 125

Asp Ala Leu Thr Lys Glu Glu Ile Glu Ala Asp Tyr Glu Gly Asn Thr
    130                 135                 140

Gly Lys Thr Ile Val Lys Thr Phe Gln Glu Arg Gly Leu Asp Tyr Glu
145                 150                 155                 160

Ala Val Pro Ala Ser Leu Val Ser Gln His Gly Pro Phe Ala Trp Gly
                165                 170                 175

Pro Thr Pro Ala Lys Ala Val Tyr Asn Ala Lys Val Leu Glu Val Val
            180                 185                 190

Ala Glu Glu Asp Tyr His Thr Ala Gln Leu Thr Arg Ala Ser Ser Glu
        195                 200                 205

Leu Pro Gln Tyr Leu Leu Asp Lys His Tyr Leu Arg Lys His Gly Ala
```

210                 215                 220
Ser Ala Tyr Tyr Gly Gln Asn Asn Ala His Ser Lys Asp His Ala Val
225                 230                 235                 240

Arg Lys

<210> SEQ ID NO 8
<211> LENGTH: 437
<212> TYPE: PRT
<213> ORGANISM: Piromyces sp. E2
<220> FEATURE:
<221> NAME/KEY: MISC_FEATURE
<222> LOCATION: (1)..(437)
<223> OTHER INFORMATION: Piromyces sp. E2 Xylose isomerase (XylA)

<400> SEQUENCE: 8

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

```
Gln Ala Trp Met Glu Ile Ile Arg Gly Gly Phe Val Thr Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
                355                 360                 365

Glu Asn Ala Ala Lys Leu Leu Gln Glu Ser Pro Tyr Thr Lys Met Lys
            370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
            435
```

<210> SEQ ID NO 9
<211> LENGTH: 600
<212> TYPE: PRT
<213> ORGANISM: Saccharomyces cerevisiae
<220> FEATURE:
<221> NAME/KEY: MISC_FEATURE
<222> LOCATION: (1)..(600)
<223> OTHER INFORMATION: S. cerevisiae Xylulokinase (Xks1p)

<400> SEQUENCE: 9

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
```

Arg Lys Phe Ser Asp Glu Leu Leu His Leu Ile Asp Ser Ser Lys
            245                 250                 255

Asp Lys Thr Ile Arg Gln Lys Leu Met Arg Ala Pro Met Lys Asn Leu
        260                 265                 270

Ile Ala Gly Thr Ile Cys Lys Tyr Phe Ile Glu Lys Tyr Gly Phe Asn
            275                 280                 285

Thr Asn Cys Lys Val Ser Pro Met Thr Gly Asp Asn Leu Ala Thr Ile
        290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
            325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Thr
370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
            405                 410                 415

Ile Asn Lys Arg Val Ile Phe Asn Pro Lys Thr Gly Met Ile Glu Arg
        420                 425                 430

Glu Val Ala Lys Phe Lys Asp Lys Arg His Asp Ala Lys Asn Ile Val
            435                 440                 445

Glu Ser Gln Ala Leu Ser Cys Arg Val Arg Ile Ser Pro Leu Leu Ser
        450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
            485                 490                 495

Pro Glu Arg Thr Phe Phe Val Gly Gly Ala Ser Lys Asn Asp Ala Ile
        500                 505                 510

Val Lys Lys Phe Ala Gln Val Ile Gly Ala Thr Lys Gly Asn Phe Arg
            515                 520                 525

Leu Glu Thr Pro Asn Ser Cys Ala Leu Gly Gly Cys Tyr Lys Ala Met
        530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
            565                 570                 575

Val Asp Asn Glu Asn Trp Asp Arg Tyr Asn Ser Lys Ile Val Pro Leu
        580                 585                 590

Ser Glu Leu Glu Lys Thr Leu Ile
            595                 600

<210> SEQ ID NO 10
<211> LENGTH: 567
<212> TYPE: PRT
<213> ORGANISM: Saccharomyces cerevisiae
<220> FEATURE:
<221> NAME/KEY: MISC_FEATURE
<222> LOCATION: (1)..(567)

<223> OTHER INFORMATION: S. cerevisiae Hxt11p amino acid sequence

<400> SEQUENCE: 10

```
Met Ser Gly Val Asn Thr Ser Ala Asn Glu Leu Ser Thr Thr Met
1               5                   10                  15

Ser Asn Ser Asn Ser Ala Val Gly Ala Pro Ser Val Lys Thr Glu His
            20                  25                  30

Gly Asp Ser Lys Asn Ser Leu Asn Leu Asp Ala Asn Glu Pro Pro Ile
            35                  40                  45

Asp Leu Pro Gln Lys Pro Leu Ser Ala Tyr Thr Thr Val Ala Ile Leu
    50                  55                  60

Cys Leu Met Ile Ala Phe Gly Gly Phe Ile Phe Gly Trp Asp Thr Gly
65                  70                  75                  80

Thr Ile Ser Gly Phe Val Asn Leu Ser Asp Phe Ile Arg Arg Phe Gly
                85                  90                  95

Gln Lys Asn Asp Lys Gly Thr Tyr Tyr Leu Ser Lys Val Arg Met Gly
                100                 105                 110

Leu Ile Val Ser Ile Phe Asn Ile Gly Cys Ala Ile Gly Gly Ile Val
            115                 120                 125

Leu Ser Lys Val Gly Asp Ile Tyr Gly Arg Arg Ile Gly Leu Ile Thr
    130                 135                 140

Val Thr Ala Ile Tyr Val Val Gly Ile Leu Ile Gln Ile Thr Ser Ile
145                 150                 155                 160

Asn Lys Trp Tyr Gln Tyr Phe Ile Gly Arg Ile Ile Ser Gly Leu Gly
                165                 170                 175

Val Gly Gly Ile Ala Val Leu Ser Pro Met Leu Ile Ser Glu Val Ala
            180                 185                 190

Pro Lys His Ile Arg Gly Thr Leu Val Gln Leu Tyr Gln Leu Met Gly
            195                 200                 205

Thr Met Gly Ile Phe Leu Gly Tyr Cys Thr Asn Tyr Gly Thr Lys Asn
    210                 215                 220

Tyr His Asn Ala Thr Gln Trp Arg Val Gly Leu Gly Leu Cys Phe Ala
225                 230                 235                 240

Trp Ala Thr Phe Met Val Ser Gly Met Met Phe Val Pro Glu Ser Pro
                245                 250                 255

Arg Tyr Leu Ile Glu Val Gly Lys Asp Glu Glu Ala Lys Arg Ser Leu
            260                 265                 270

Ser Lys Ser Asn Lys Val Ser Val Asp Asp Pro Ala Leu Leu Val Glu
            275                 280                 285

Tyr Asp Thr Ile Lys Ala Gly Ile Glu Leu Glu Lys Leu Ala Gly Asn
    290                 295                 300

Ala Ser Trp Ser Glu Leu Leu Ser Thr Lys Thr Lys Val Phe Gln Arg
305                 310                 315                 320

Val Leu Met Gly Val Met Ile Gln Ser Leu Gln Gln Leu Thr Gly Asp
                325                 330                 335

Asn Tyr Phe Phe Tyr Tyr Gly Thr Thr Ile Phe Lys Ser Val Gly Leu
            340                 345                 350

Lys Asp Ser Phe Gln Thr Ser Ile Ile Ile Gly Val Val Asn Phe Phe
            355                 360                 365

Ser Ser Phe Ile Ala Val Tyr Thr Ile Glu Arg Phe Gly Arg Arg Thr
    370                 375                 380

Cys Leu Leu Trp Gly Ala Ala Ser Met Leu Cys Cys Phe Ala Val Phe
385                 390                 395                 400
```

-continued

```
Ala Ser Val Gly Val Thr Lys Leu Trp Pro Gln Gly Ser Ser His Gln
            405                 410                 415
Asp Ile Thr Ser Gln Gly Ala Gly Asn Cys Met Ile Val Phe Thr Met
            420                 425                 430
Phe Phe Ile Phe Ser Phe Ala Thr Thr Trp Ala Gly Gly Cys Tyr Val
            435                 440                 445
Ile Val Ser Glu Thr Phe Pro Leu Arg Val Lys Ser Arg Gly Met Ala
            450                 455                 460
Ile Ala Thr Ala Ala Asn Trp Met Trp Gly Phe Leu Ile Ser Phe Phe
465                 470                 475                 480
Thr Pro Phe Ile Thr Gly Ala Ile Asn Phe Tyr Tyr Gly Tyr Val Phe
            485                 490                 495
Leu Gly Cys Leu Val Phe Ala Tyr Phe Tyr Val Phe Phe Phe Val Pro
            500                 505                 510
Glu Thr Lys Gly Leu Thr Leu Glu Glu Val Asn Thr Met Trp Leu Glu
            515                 520                 525
Gly Val Pro Ala Trp Lys Ser Ala Ser Trp Val Pro Pro Glu Arg Arg
            530                 535                 540
Thr Ala Asp Tyr Asp Ala Asp Ala Ile Asp His Asp Asn Arg Pro Ile
545                 550                 555                 560
Tyr Lys Arg Phe Phe Ser Ser
            565
```